United States Patent [19]

Lok

[11] 4,234,498
[45] Nov. 18, 1980

[54] PREPARATION OF GLYCERIDE ESTERS

[75] Inventor: Cornelis M. Lok, Rockanje, Netherlands

[73] Assignee: Lever Brothers Company, New York, N.Y.

[21] Appl. No.: 75,572

[22] Filed: Sep. 14, 1979

[30] Foreign Application Priority Data

Sep. 19, 1978 [GB] United Kingdom ............... 37337/78

[51] Int. Cl.$^3$ ......................... C11C 3/02; C07C 69/73; C07C 69/66
[52] U.S. Cl. .............................. 260/410.7; 260/410.8; 560/181; 560/182
[58] Field of Search ......................... 260/410.7, 410.8; 560/181, 182

[56] References Cited

U.S. PATENT DOCUMENTS

| | | | |
|---|---|---|---|
| 2,523,309 | 9/1950 | Kester | 260/410.7 |
| 2,695,915 | 11/1954 | DeGroote | 560/182 |
| 2,910,490 | 10/1959 | Malkemus | 260/410.7 |
| 3,251,870 | 5/1966 | Dalby | 260/410.7 |
| 3,796,736 | 3/1974 | Mitchell | 260/410.8 |
| 3,845,087 | 10/1974 | DeGroote | 260/410.7 |
| 4,025,540 | 5/1977 | Kleemann et al. | 260/410.7 |
| 4,154,749 | 5/1979 | Klawack | 260/410.7 |

*Primary Examiner*—John F. Niebling
*Attorney, Agent, or Firm*—Melvin H. Kurtz

[57] ABSTRACT

The invention concerns the preparation of glycerides in which glycidol is reacted with a fatty acid, first in the form of the anhydride to produce the corresponding epoxy glyceride or glycidol ester, at the same time liberating free fatty acid from the anhydride and thereafter continuing reaction, this time between the liberated free fatty acid or another acid, in the presence of an acylation catalyst under the influence of which the oxirane ring is ruptured and diglycerides produced. These may be used in the preparation of synthetic fats.

28 Claims, No Drawings

PREPARATION OF GLYCERIDE ESTERS

GENERAL DESCRIPTION OF THE INVENTION

Glycidol may be considered as a dehydrated glycerol and possesses properties making it an ideal glyceride precursor. The epoxy group provides the possibility of selectively introducing different fatty acids and the absence of substituents such as chlorine which are undesired from a toxicological point of view, makes it a relatively safe precursor for glycerides intended for edible purposes. Thus glycidol possesses the same flexibility as epichlorohydrin, but without several of its technical and toxicological objections. The price of glycidol has been rather high in the past and its applications therefore have been confined to pharmaceutical and chemical uses. This situation will shortly change when it will be available on a large scale at relatively low prices and will attract attention as a starting material for di- and triglycerides.

While glycidol with its two functional groups shows many reactions, only a few of these are relevant for the synthesis of glyceride-type products. It is esterified with acid chlorides which, however, also attack the epoxy ring to yield monochlorohydrin monoesters, or diesters when excess acyl chloride is used. Several glycidol esters can be prepared using triethylamine or pyridine as a hydrogen chloride acceptor but the reaction has received litte attention because glycidol esters have been more accessible from epichlorohydrin, available in bulk quantities. In the preparation of glycidol esters from epichlorohydrin with sodium salts of fatty acids chlorohydrin esters must be removed, e.g. by molecular distillation or crystallisation and a massive excess of epichlorohydrin is required otherwise yield decreases and the reaction mixture becomes very difficult to handle. The further esterification of glycidol esters provides a controlled progressive acylation operation to diglycerides which by solid-state isomerisation may be converted to the pure 1,3-diglyceride, thus providing a route to triglycerides in which the position of each added acyl group on the glyceride residue is unequivocally controlled. Compared with the epichlorohydrin route the new process possesses the following advantages:-

The molar ratio of the reactants is about 1:1 compared with a fifteen-fold excess of epichlorohydrin, making a recirculation step unnecessary.

Glycidol is a much safer compound than epichlorohydrin. In addition, no chlorine-containing by-products are produced in the process. Chlorohydrin esters are undesirable by-products both in the reaction of epichlorohydrin with soaps and in the esterification of glycidol with acid chlorides.

The operation of the process is easy to perform and takes less time. No crystallisation or distillation step is needed after the first step.

Yields are at least as high as in the epichlorohydrin process.

PRIOR ART

F. Zetsche and F. Aeschlimann, Helv. Chim. Acta 9 (1926) 708 disclosed that glycidol is esterified with acid chlorides which also attack the epoxy ring to yield monochlorohydrin monoesters, or diesters when excess acyl chloride is used.

A. Bigot, Ann. Chim. Phys. 22 (1891) 433 observed that acyl chlorides could add to the epoxy group of epichlorohydrin to produce dichloropropanol esters.

E. B. Kester, C. J. Gaiser and M. E. Lazar, J. Org. Chem. 8 (1943) 550 reacted glycidol with acid chlorides using triethylamine or pyridine as hydrogen chloride acceptors.

The addition of fatty acids to glycidol esters disclosed in U.S. Pat. No. 2,523,309 is improved using onium catalysts according to Dutch Pat. No. 71.03013. The synthesis of glycerides from the reaction of glycidol with fatty acid anhydrides has however nowhere been disclosed as an operation in successive stages.

DETAILED DESCRIPTION OF THE INVENTION

This invention relates to the preparation of esters, specifically glycerides, from glycidol.

According to British Patent No. 1,325,924 high yields of diglycerides may be obtained by heating a fatty glycidol ester with a fatty acid in the presence of a quaternary onium salt. It has now been found that glycidol esters and fatty acids may be obtained in good yield by reaction between glycidol and the anhydride of the fatty acid.

Accordingly, the present invention provides a process for the preparation of diglycerides by glycidol acylation in which a substantial amount of glycidol ester is produced in a first stage using an acid anhydride as the acylation agent under conditions in which the oxirane ring is preserved before diglycerides are produced in a second stage by acylation of the oxirane ring of the glycidol ester.

The glycidol ester may be separated from the fatty acid by-product of the anydride to recover the ester. A particular advantage of the invention is however that further esterification may take place, by reaction between the newly-formed glycidol ester and free ffatty acid generated as a by-product from the anhydride, without necessarily effecting an intermediate refining step to recover the glycidol ester. Working in this way the two acyl radicals of the diglyceride product obtained are the same and all that is necessary is to change the reaction conditions whereby the further esterification can be continued with opening of the oxirane ring in the presence of the free fatty acid. Where different acyl radicals of the diglyceride are required at least part of the fatty acid by-product should be replaced by the different fatty acid required in the reaction medium.

The necessary change in conditions to effect the further esterification of the glycidol ester may be effected for example by introducing a quaternary onium salt and operating preferably as described in the above patent case when the formation of the glycidol ester is substantially complete.

Although other quaternary onium salts such as quaternary phosphonium salts can be used, quaternary ammonium salts are preferred, for example tetraethyl ammonium acetate, benzylcetyldimethylammonium chloride and choline chloride. Preferably the catalyst concentration is from 0.005 to 0.05, more preferably 0.02 to 0.05, moles per mole of glycidol ester. It is essential however to avoid reproducing these conditions in the first stage, thereby ensuring that the epoxy ring remains largely intact in that stage. In particular the glycidol should be purified to ensure that it is free from impurities which could serve to catalyse ring-opening in the first stage. Temperature and time of reaction in the first stage should also be selected for the first stage in keeping with the object of retaining the epoxy ring intact. In solvents the first stage temperature should preferably not exceed 150° C., preferably 80° to 120° C., for a period preferably not more than 8 hours, particularly 2 to 6 hours. In the absence of solvent the first stage reaction temperature should preferably not exceed 100° C., preferably 60° to 80° C. and preferably for a period not exceeding 6 hours, preferably 2 to 4 hours. The reaction time in the first stage for completion also varies according to concentration in the solvent; with 5:1 solvent:anhydride weight ratio using 100° to 140° C. petroleum ether 5 hours is adequate, within a range from 3 to 7 hours. For the ratio 2:1 reaction is complete in about 2 hours, with a glycidol excess in both cases of 10 to 15% preferably, in a range 5 to 50%.

Preferably an at least equimolar ratio of glycidol and anhydride is used in the process according to the invention. Two moles of free fatty acid are liberated by each mole of anhydride and is sufficient at least in theory to convert the glycidol ester to diglyceride if this is subsequently desired, but it is further preferred to operate with a slight excess of glycidol, e.g. to 10% molar excess since the diglyceride end-product is then easier to purify and the reaction proceeds more readily to completion. Up to 50% excess may be used, but above this significant amounts of openring monoglycerides appear. Either of the two stages may be carried out in an inert solvent, preferably under reflux, particularly in a hydrocarbon, for example toluene or preferably a light petroleum of boiling point 100° to 140° C., or halohydrocarbon e.g. chlorobenzene. The reaction may however be slower, particularly the second stage which is preferably carried out without solvent. A solvent is preferred for the first stage since somewhat less impurities are produced.

It is of course convenient to carry out both stages of the process according to the invention in the same solvent, if it is intended to use a solvent in both; a solvent:anydride weight ratio of 1:1 to 20:1, especially about 5:1, is preferred. Either stage may be carried out using an inert gas blanket where this may be desirable, e.g. to protect unsaturated acids from deterioration by oxidation, and in general it is preferable to agitate the reactants in both stages.

The esters produced by the present invention are preferably of fatty acids having from 2 to 22 carbon atoms, particularly those found in natural fats and especially those having from 10 to 22 carbon atoms, more especially the saturated and unsaturated $C_{16}$ and $C_{18}$ fatty acids. The important feature of the preparation of diglycerides in accordance with the present invention is the substantial absence of further esterification during the reaction, to form triglycerides, with the effect that the diglycerides may be recovered in high yields without difficulty. This aspect of the invention is of particular importance for the preparation from these diglycerides of symmetrical disaturated triglycerides. These are highly prized for their melting performance, those of $C_{16}$ and $C_{18}$ fatty acids being akin to this and other aspects to those found in cocoabutter and other expensive tropical fats used in chocolate. In their preparation diglycerides of palmitic and/or stearic acid prepared in accordance with the invention may first be isomerised to produce a maximum yield of the 1,3-isomer, following for example the procedure described in U.S. Patent No. 3,845,087 and this then further esterified in the remaining 2-position of the glyceride structure by oleic acid or acylating agent. In that event preferably the onium catalyst used in the second stage is left in the product to catalyse the isomerisation.

The acid residues of the acylation reagents in the first and second stages may be the same, in which case the second stage may proceed between the products of the first stage, i.e. acid and glycidol ester. Alternatively, an additional acid may be added at the second stage to give mixed diglycerides, or the acid product of the first stage may be removed and a different acid added, to give a diglyceride with two different acyl groups.

EXAMPLE 1

0.5 moles oleic anhydride and 0.55 moles glycidol dissolved in an approximately equal weight of petroleum fraction, boiling point 100° to 140° C., were heated with reflux for 4 hours. After cooling the mixture was diluted with a similar weight of the solvent and washed several times with a mixture of 3 parts methanol per part of water by volume using for each wash a quantity of about 20% by volume of the petroleum mixture. The first 3 washes contained in addition 0.5 moles per liter of ammonia to neutralise the oleic acid liberated during esterification of the glycidol.

The washed petroleum mixture was dried over magnesium sulphate and the solvent evaporated, leaving 170 grams of crude glycidol oleate corresponding to 100% yield and found by thin layer chromatography analysis to be more than 90% pure, the main contaminants being diglycerides. Then 0.46 moles of stearic acid and 0.015 moles of tetraethylammonium bromide were added and the mixture was heated at 100° C. for 3 hours with agitation under an inert gas blanket. The mixture of diglyceride isomers obtained was then heated in the solid state at 38° to 40° C. for 5 days in order to convert the 1,2-diglycerides into the 1,3-isomer. This was then crystallised from three times its weight of acetone at 0° C. The yield of 1-oleoyl-3-stearoylglycerol was 60% from an initial yield before recrystallisation of 80 to 85%.

The oleic acid liberated was recovered by acidifying the wash mixtures with 6M hydrochloric acid and extracting with light petroleum. The petroleum extracts were then washed with water and after drying over magnesium sulphate yielded 86% crude oleic acid.

EXAMPLE 2

0.53 moles of oleic anhydride and 0.58 moles of glycidol were dissolved in approximately twice their total volume of light petroleum of boiling point 80° to 100° C. refluxed for 7 hours. The solvent was then removed by evaporation and heating at 90° C. under 0.2 mm Hg pressure. Approximately 0.015 moles of tetraethylammonium bromide was added to the mixture of glycidol oleate and oleic acid obtained which was then heated at 105° C. for 3 hours. The mixture was then recrystallised from 10 times its weight of acetone at −30° C. when 182.5 grams of 1,3-dioleine was obtained, corresponding to a yield of 56%. The mother liquor contained mainly 1,2-dioleine in addition to some mono-oleine and trioleine. The mother liquor was further heated at 100° C. to achieve equilibrium between the 1,2- and 1,3-dioleines and a further 30 grams of the 1,3-isomer was then recovered from it by crystallisation.

EXAMPLE 3

0.1 moles of palmitic anhydride were heated with 0.12 moles of glycidol in approximately 2 moles of toluene under reflux for 5 hours, after which no anhydride could be detected in the mixture by thin layer chromatography.. The toluene was evaporated off and final traces of excess glycidol removed by heating to 100° C. in 0.2 mm Hg pressure. After adding 0.003 moles tetraethylammonium bromide the crude glycidol palmitate product was heated with stirring at 110° C. for 4 hours. The mixture of dipalmitate isomers first obtained was cooled to solidify and heated in the solid state at 65° C. for 48 hours in order to convert the 1,2-isomer present to the 1,3-form. This was then cooled and crystallised from 5 times its weight of acetone at room temperature, approximately 15° C. The yield of 1,3-dipalmitate, which was between 98 and 99% pure, was 90%.

EXAMPLE 4

0.45 moles of stearic anhydride and 0.5 moles glycidol were heated together at 70° C. for 2½ hours, after which time all the anhydride had reacted. 0.015 moles of tetraethylammonium bromide was added to the crude glycidol stearate obtained and the mixture heated for 2 hours at 110° C. After cooling until solid the mixture was isomerised in the solid state by heating at 65° C. for 2 days and the resulting product crystallised from a mixture of 9 parts acetone per part of light petroleum by volume at room temperature, yielding 80% of the 1,3-distearate isomer.

EXAMPLE 5

0.5 moles of palmitic anhydride and 0.6 moles of glycidol in 1.2 l. light petroleum of boiling point 100° to 140° C. were refluxed for 5 hours. After cooling the mixture was washed several times with a solution of 0.5 moles/l. ammonia in methanol/water 3/1. by volume until all free fatty acid had been removed. Then the washing was repeated with a mixture of methanol/water 3/1. by volume alone. The petroleum solution was dried over magnesium sulphate and the solvent evaporated. The crude glycidol palmitate, which contained small amounts of dipalmitate and tripalmitate, was purified by molecular distillation at 160° C. (1 mmHg pressure). To the distillate 0.4 moles of stearic acid and 0.008 moles of choline chloride was added and the mixture was heated at 120° C. for 4 hours. The resulting diglyceride mixture was isomerised in the solid state just below the melting point of the mixture for 48 hours and crystallised from 5 times its weight of acetone at 150° C. The yield of pure 1-palmitoyl-3-stearoylglycerol was 72%.

EXAMPLE 6

0.5 moles of palmitic anhydride and 0.6 moles of glycidol in 1.2 l. dry 1,4-dioxane were refluxed for 11 hours. The solvent was then removed by evaporation and heating at 80° C. under 1 mm Hg pressure for 1 hour. Approximately 0.015 moles of tetraethylammonium bromide was added to the glycidol ester/fatty acid mixture which was then heated at 120° C. for 1.2 hours. The mixture of dipalmitate isomers was cooled and isomerised in the solid state by heating at 65° C. for 48 hours. This was then cooled and crystallised from six times its weight of light petroleum, toluene, alcohol mixture (ratio 10/4/1) at room temperature. The yield of pure 1,3-dipalmitate was 84%.

Using isobutyl methyl ketone a reaction time of 7 hours in the first step was sufficient and a yield of 85% was obtained.

What is claimed is:

1. Process for the preparation of diglycerides by glycidol acylation in which a substantial amount of glycidol ester is produced in a first stage using an acid anhydride as the acylation agent under conditions in which the oxirane ring is preserved before diglycerides are produced in a second stage by acylation of the oxirane ring of the glycidol ester.

2. Process according to claim 1 in which the molar ratio glycidol to anhydride, at least in the first stage, is up to 50% in excess of unity.

3. Process according to claim 1 in which the molar ratio glycidol to anhydride, at least in the first stage, is up to 10% in excess of unity.

4. Process according to claim 1 in which at least the first stage is carried out in a solvent at a temperature not in excess of 150° C.

5. Process according to claim 4 which is carried out at a temperature from 80° to 120° C.

6. Process according to claim 5 in which the solvent: anhydride ratio is from 1:1 to 20:1 by weight.

7. Process according to claim 6 in which the said ratio is approximately 5:1 by weight.

8. Process according to claim 4 in which a hydrocarbon is used as solvent.

9. Process according to claim 8 in which the hydrocarbon comprises a petroleum fraction.

10. Process according to claim 8 in which the hydrocarbon comprises an aromatic hydrocarbon.

11. Process according to claim 4 in which the first stage is carried out for a period of not more than 8 hours.

12. Process according to claim 11 in which the reaction is carried out for a period from 2 to 6 hours.

13. Process according to claim 1 in which the first stage is carried out in the absence of a solvent at a reaction temperature not in excess of 100° C.

14. Process according to claim 13 in which the first stage reaction temperature is between 60° and 80° C.

15. Process according to claim 13 in which the first stage is carried out for a period not exceeding 6 hours.

16. Process according to claim 15 in which the first stage is carried out for a period from 2 to 4 hours.

17. Process according to claim 1 wherein the second stage is carried out in the absence of solvent.

18. Process according to claim 1 wherein the fatty acid residue of the acylation agent in both stages comprises at least one fatty acid having from 10 to 22 carbon atoms.

19. Process according to claim 18 wherein the fatty acid comprises a saturated or unsaturated $C_{16}$ or $C_{18}$ fatty acid.

20. Process according to claim 18 wherein the acylation reagent in the second stage comprises the fatty acid product of the first stage.

21. Process according to claim 1 wherein the acylation agent in the second stage comprises a fatty acid added to the glycidol ester.

22. Process according to claim 21 wherein the fatty acid product of the first stage is first removed.

23. Process according to claim 1 wherein the second stage is carried out in the presence of an onium catalyst.

24. Process according to claim 23 wherein the catalyst comprises a tetraalkylammonium halide.

25. Process according to claim 24 wherein the amount of catalyst present is from 0.005 to 0.05 moles per mole of glycidol used in the preparation of the glycidol ester.

26. Process according to claim 1 wherein diglyceride recovered from the second stage is heated in the solid state to convert 1,2-isomer present to the 1,3-isomer.

27. Process according to claim 26 wherein an onium catalyst used in the second stage is retained in the diglyceride to catalyse the said isomerisation.

28. Process according to claim 1 wherein glycidol is heated in an approximately 10% molar excess with a $C_{16}$–$C_{18}$ fatty acid anhydride in the first stage in a hydrocarbon solvent in a weight concentration of the reactants in the solvent from 20 to 100%, at a temperature from 80° to 140° C. for a period not exceeding 8 hours and after removing solvent, for a further 2 to 4 hours in the second stage from 100° to 120° C. in the presence of from 0.02 to 0.05 moles of tetraalkylammonium bromide per mole of glycidol ester and further heating the diglycerides obtained in the solid state to effect conversion to the 1,3-isomer.

* * * * *